United States Patent [19]

Capet et al.

[11] Patent Number: 5,637,602

[45] Date of Patent: Jun. 10, 1997

[54] PYRROLIDINE AND THIAZOLIDINE DERIVATIVES, THEIR PREPARATION AND DRUGS CONTAINING SAME

[75] Inventors: Marc Capet, Thiais; Marie-Christine Dubroeucq, Enghein les Bains; Franco Manfre, Limeil-Brevannes; Jean-Paul Martin, Colombes, all of France

[73] Assignee: Rhone-Poulenc Rorer S.A., Antony, France

[21] Appl. No.: 448,405

[22] PCT Filed: Jan. 3, 1994

[86] PCT No.: PCT/FR94/00006

§ 371 Date: Jun. 7, 1995

§ 102(e) Date: Jun. 7, 1995

[87] PCT Pub. No.: WO94/15954

PCT Pub. Date: Jul. 21, 1994

[30] Foreign Application Priority Data

Jan. 7, 1993 [FR] France .................... 93 00075

[51] Int. Cl.$^6$ .................... C07D 227/10; A61K 31/40
[52] U.S. Cl. ............................. 514/365; 548/200
[58] Field of Search ................ 514/365; 548/200

[56] References Cited

FOREIGN PATENT DOCUMENTS

WO91/13862  9/1991  WIPO .
WO93/01167  1/1993  WIPO .

*Primary Examiner*—Robert Gerstl
*Attorney, Agent, or Firm*—Finnegan, Henderson, Farabow, Garrett & Dunner, L.L.P.

[57] ABSTRACT

This invention relates to a compound of formula (I), their salts, the preparation thereof and drugs containing same. The compounds of formula (I) have interesting pharmacological properties. Said compounds have a high affinity for chloecystokinin (CCK) and gastrin receptors and are therefore useful in the treatment and prevention of CCK and gastrin-related disorders affecting the nervous system and gastrointestinal tract.

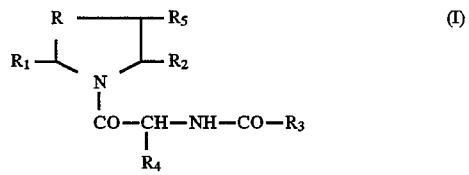

5 Claims, No Drawings

PYRROLIDINE AND THIAZOLIDINE DERIVATIVES, THEIR PREPARATION AND DRUGS CONTAINING SAME

DESCRIPTION OF THE INVENTION

The present invention relates to derivatives of formula:

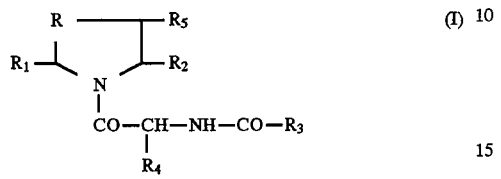

their salts, their preparation and the medications containing them.

In formula (I), either R denotes a methylene, ethylene, SO, $SO_2$ or CHOH radical or a sulphur atom, $R_1$ denotes a pyridyl radical optionally substituted by one or more alkyl radicals, furyl optionally substituted by one or more alkyl radicals, thienyl optionally substituted by one or more alkyl radicals, quinolyl optionally substituted by one or more alkyl radicals, naphthyl optionally substituted by one or more alkyl radicals, indolyl optionally substituted by one or more alkyl radicals or phenyl optionally substituted by one or more substituents chosen from halogen atoms and alkyl, alkoxy, hydroxyl, nitro, amino, monoalkylamino, dialkylamino, alkoxycarbonyl, $-CO-NR_7R_8$, $-NH-CO-CH_3$, trifluoromethyl or trifluoromethoxy radicals, and $R_5$ denotes a hydrogen atom, or R denotes a methylene radical, $R_1$ denotes a hydrogen atom and $R_5$ denotes a phenyl radical, or R denotes a radical $CHR_6$, each of $R_1$ and $R_5$ denoting a hydrogen atom, $R_2$ denotes an alkoxycarbonyl, cycloalkoxycarbonyl, cycloalkylalkoxycarbonyl, $-CONR_9R_{10}$ or phenyl radical optionally substituted by one or more substituents chosen from alkyl, alkoxy or hydroxyl radicals, $R_3$ denotes a phenylamino radical in which the phenyl nucleus is substituted by one or more substituents chosen from the radicals -alk-$SO_2$H, $-SO_2-NH-CO-R_{11}$, $-B(OH)_2$, $-SO_2-NH-SO_2-R_{11}$, $-CO-NH-CO-R_{11}$, $-CO-NH-SO_2-R_{11}$, $-C(NH_2)=NOH$, $-SO_2-NH-R_{12}$, $-CO-NH-R_{12}$,

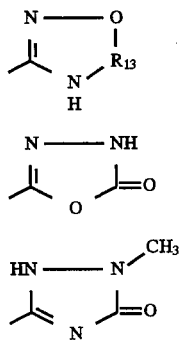

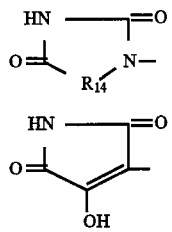

and optionally by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3$H (in salt form), —CH=CH-alk', —C(=NOH)—COOX, —S-alk-COOX, —SO-alk-COOX, —$SO_2$-alk-COOX, —O—$CH_2$-alk'-COOX, —CX=N—O-alk-COOX, -alk-N(OH)—CO-alk or 2,2-dimethyl-4,6-dioxo-1,3-dioxan-5-yl radicals, $R_4$ denotes a hydrogen atom or an alkyl radical, $R_6$ denotes a phenyl radical, $R_7$ denotes a hydrogen atom or an alkyl, phenylalkyl or phenyl radical optionally substituted by one or more substituents chosen from halogen atoms and alkyl, alkoxy and alkylthio radicals, $R_8$ denotes an alkyl, phenylalkyl or phenyl radical optionally substituted by one or more substituents chosen from halogen atoms and alkyl, alkoxy and alkylthio radicals, or else $R_7$ and $R_8$ together with the nitrogen atom to which they are attached form a saturated or unsaturated mono- or polycyclic heterocyclic ring containing 4 to 9 carbon atoms and one or more heteroatoms (O, N) and optionally substituted by one or more alkyl radicals, $R_9$ denotes a hydrogen atom or an alkyl, cycloalkylalkyl, cycloalkyl, phenylalkyl or phenyl radical optionally substituted by one or more substituents chosen from halogen atoms and alkyl, alkoxy and alkylthio radicals, $R_{10}$ denotes an alkyl, cycloalkylalkyl, cycloalkyl, phenylalkyl or phenyl radical optionally substituted by one or more substituents chosen from halogen atoms and alkyl, alkoxy and alkylthio radicals, or else $R_9$ and $R_{10}$ together with the nitrogen atom to which they are attached form a saturated or unsaturated mono- or polycyclic heterocyclic ring containing 4 to 9 carbon atoms and one or more heteroatoms (O, N, S) and optionally substituted by one or more alkyl radicals, $R_{11}$ denotes an alkyl, cycloalkyl, trifluoromethyl or phenyl radical optionally substituted by one or more substituents chosen from cyano, alkoxy, nitro and amino radicals and halogen atoms, $R_{12}$ denotes a 5-tetrazolyl radical, $R_{13}$ denotes C=O or S=O, $R_{14}$ denotes O or C=O, X denotes a hydrogen atom or an alkyl or phenylalkyl radical, alk denotes an alkyl or alkylene radical, alk' denotes a hydroxyalkyl, hydroxyalkylene, alkoxyalkyl or alkoxyalkylene radical.

In the above definitions and those which will be cited below, unless stated otherwise, the alkyl, alkylene and alkoxy radicals and the alkyl, alkylene and alkoxy parts contain 1 to 4 carbon atoms as a straight or branched chain, the acyl radicals or parts contain 2 to 4 carbon atoms and the cycloalkyl radicals and parts contain 3 to 6 carbon atoms.

When $R_7$ and $R_8$ with the nitrogen atom to which they are attached form a heterocyclic ring, the latter is preferably a piperidino ring optionally substituted by one or more alkyl radicals or a 1,2,3,4-tetrahydroquinoline ring.

When $R_9$ and $R_{10}$ with the nitrogen atom to which they are attached form a heterocyclic ring, the latter is preferably a piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring, it being possible for these rings to be optionally substituted by at least one alkyl radical.

The compounds of formula (I) containing one or a number of asymmetric centres exhibit isomeric forms. The racemates and the enantiomers of these compounds also form part of the invention.

The compounds of formula (I) in the case of which R denotes a methylene, ethylene, CHOH or CHR$_6$ radical or a sulphur atom may be prepared by the action of a reactive derivative of carbamic acid, optionally obtained in situ by the action of a reactive derivative of carbonic acid, chosen from N,N'-diimidazolecarbonyl, phosgene, diphosgene, triphosgene and p-nitrophenyl chloroformate on a derivative of formula:

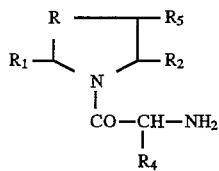
(II)

in which R denotes a methylene, ethylene, CHOH or CHR$_6$ radical or a sulphur atom and $R_1$, $R_2$, $R_4$, $R_5$ and $R_6$ have the same meanings as in formula (I), on an aniline whose phenyl nucleus is substituted by one or more substituents chosen from the radicals -alk-SO$_2$H, —SO$_2$—NH—CO—R$_{11}$, —B(OH)$_2$, —SO$_2$—NH—SO$_2$—R$_{11}$, —CO—NH—CO—R$_{11}$, —CO—NH—SO$_2$—R$_{11}$, —C(NH$_2$)=NOH, —SO$_2$—NH—R$_{12}$, —CO—NH—R$_{12}$,

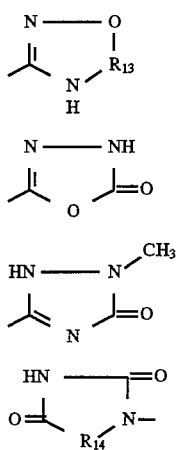

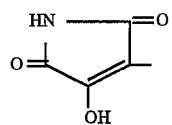

and optionally by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO$_3$H (in salt form), —CH=CH-alk', —C(=NOH)—COOX, —S-alk-COOX, —SO-alk-COOX, —SO$_2$-alk-COOX, —O—CH$_2$-alk'-COOX, —CX=N—O-alk-COOX, -alk-N(OH)—CO-alk or 2,2-dimethyl-4,6-dioxo-1,3-dioxan-5-yl radicals.

This reaction is generally performed in an inert solvent such as tetrahydrofuran, dimethylformamide, a chlorinated solvent (for example chloroform or 1,2-dichloroethane) or an aromatic solvent (for example benzene or toluene) or a mixture of these solvents, at a temperature of between 20° C. and the boiling temperature of the solvent.

The reactive derivative of carbamic acid can be obtained in the same solvent and temperature conditions.

The derivatives of formula (II) can be obtained by deprotection of a derivative of formula:

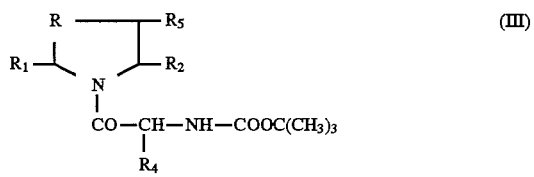
(III)

in which R denotes a methylene, ethylene, CHOH or CHR$_6$ radical or a sulphur atom and $R_1$, $R_2$, $R_4$, $R_5$ and $R_6$ have the same meanings as in formula (I).

This deprotection is preferably performed by means of iodotrimethylsilane or trifluoroacetic acid, in an inert solvent such as acetonitrile or a chlorinated solvent (for example chloroform or 1,2-dichloroethane) at a temperature of between 15° and 40° C.

The derivatives of formula (III) can be obtained by the action of a derivative of formula:

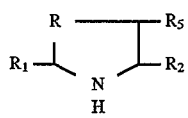
(IV)

in which R denotes a methylene, ethylene, CHOH or CHR$_6$ radical or a sulphur atom and $R_1$, $R_2$, $R_5$ and $R_6$ have the same meanings as in formula (I), on an acid of formula:

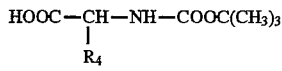
(V)

in which $R_4$ is defined as in formula (I).

This reaction is performed in an inert solvent such as acetonitrile, tetrahydrofuran or a chlorinated solvent, in the presence of a condensing agent employed in peptide chemistry such as a carbodiimide (for example N,N'-dicyclohexylcarbodiimide) or an alkyl chloroformate, at a temperature of between 10° and 40° C.

The derivatives of formula (V) can be obtained by the usual methods for protecting amino acids.

The derivatives of formula (IV) can be prepared by application or adaptation of the methods described in the literature and of the methods described below.

The derivatives of formula (IV) in which $R_2$ denotes an alkoxycarbonyl, cycloalkoxycarbonyl or cycloalkylalkoxycarbonyl radical can be obtained by esterification of an acid of formula:

(VI)

in which R denotes a methylene, ethylene, CHOH or $CHR_6$ radical or a sulphur atom and $R_1$, $R_5$ and $R_6$ have the same meanings as in formula (I).

This esterification is generally performed by means of an alcohol $R_{15}$—OH in which $R_{15}$ denotes an alkyl, cycloalkyl or cycloalkylalkyl radical, in acidic medium, at the boiling temperature of the reaction mixture. In the case of the compounds of formula (IV) in which $R_2$ denotes a tert-butoxycarbonyl radical, isobutene is reacted with a product of formula (VI) in an inert solvent such as a chlorinated solvent, in the presence of an acid such as sulphuric acid, at a temperature close to 20° C.

The derivatives of formula (VI) in which R denotes a methylene radical, $R_1$ is defined as in formula (I) and $R_5$ denotes a hydrogen atom can be prepared by application or adaptation of the method described by H. Gershon et al., J. Org. Chem., 26, 2347 (1961).

The derivatives of formula (VI) in which R denotes a radical $CHR_6$ and $R_1$, $R_5$ and $R_6$ are defined as in formula (I) can be prepared by application or adaptation of the method described by J. K. Thottathil et al., Tetrahedron Letters, 27, 151 (1986) and D. R. Kronenthal et al., Tetrahedron Letters, 31, 1241 (1990).

The derivatives of formula (VI) in which R denotes a methylene radical, $R_1$ denotes a hydrogen atom and $R_5$ denotes a phenyl radical can be prepared by application or adaptation of the method described by Y. N. Belokon et al., J. Chem. Soc. Perkin Trans. 1, 2075 (1988) and J. Rivier and G. R. Marshall, Peptides, Chemistry, Structure and biology, Proceedings of the Eleventh American Peptide Symposium, Jul. 9–14, 1989—La Jolla Calif. U.S.A.—ESCOM Leiden 1990.

The derivatives of formula (VI) in which R denotes a sulphur atom, $R_1$ is defined as in formula (I) and $R_5$ denotes a hydrogen atom can be obtained by the action of a derivative of formula:

(VII)

in which $R_5$ denotes a hydrogen atom, on an aldehyde of formula:

(VIII)

in which $R_1$ has the same meanings as in formula (I).

This reaction is preferably performed in an alcohol at the boiling temperature of the reaction mixture.

The derivatives of formula (VI) in which R denotes an ethylene radical, $R_1$ is defined as in formula (I) and $R_5$ denotes a hydrogen atom can be prepared by reduction of the derivatives of formula:

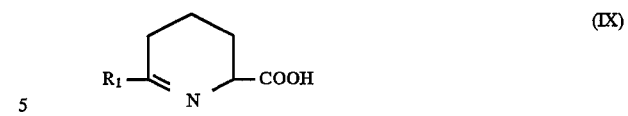

(IX)

in which $R_1$ has the same meanings as in formula (I).

This reduction is generally performed using hydrogen in an inert solvent such as an alcohol, in the presence of a catalyst such as platinum oxide, at a temperature of between 20° and 100° C., optionally under pressure or by means of sodium borohydride and potassium carbonate in a water-alcohol (preferably ethanol) mixture at a temperature of between 0° and 20° C.

The derivatives of formula (IX) can be obtained by the action of an alkyl acetamidomalonate on a derivative of formula:

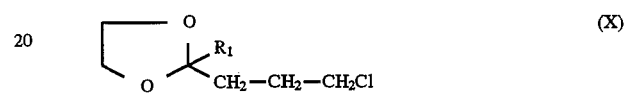

(X)

in which $R_1$ has the same meanings as in formula (I), followed by the hydrolysis, decarboxylation and dehydration of the product obtained, the operation being carried out by heating in aqueous hydrochloric acid, the action of the alkyl acetamidomalonate on the product of formula (X) being performed in an alcohol, in the presence of a base such as an alkali metal alcoholate, at the boiling temperature of the solvent.

The derivatives of formula (X) can be obtained by application or adaptation of the method described by M. T. Wills et al., J. Org. Chem., 45 (12), 2495 (1980).

The derivatives of formula (IV) can also be obtained by deprotection of a derivative of formula:

(XI)

in which R denotes a methylene, ethylene, CHOH or $CHR_6$ radical or a sulphur atom, $R_1$, $R_2$, $R_5$ and $R_6$ have the same meanings as in formula (I) and Z denotes an alkyl and preferably tert-butyl radical, it being understood that when $R_2$ denotes a tert-butoxycarbonyl radical, Z cannot be methyl or ethyl.

This reaction is performed in an inert solvent such as a chlorinated solvent, by means of iodotrimethylsilane at a temperature of between 15° C. and the boiling temperature of the reaction mixture.

The derivatives of formula (XI) in which R denotes a methylene radical, $R_1$ denotes a phenyl, optionally substituted 2-thienyl, optionally substituted 2-furyl or optionally substituted 3-indolyl radical, $R_2$ denotes an alkoxycarbonyl, cycloalkoxycarbonyl or cycloalkylalkoxycarbonyl radical and $R_5$ denotes a hydrogen atom can be obtained by the action of a derivative of formula:

(XII)

in which $R_1$ denotes a phenyl, optionally substituted 2-thienyl, optionally substituted 2-furyl or optionally substituted 3-indolyl radical, on a derivative of formula:

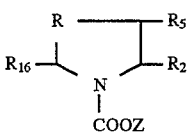

in which R denotes a methylene radical, $R_2$ and $R_5$ have the same meanings as above, $R_{16}$ denotes an alkoxy radical containing 1 or 2 carbon atoms and Z denotes an alkyl radical.

This reaction is generally performed in the presence of a strong acid such as p-toluenesulphonic acid or a Lewis acid such as aluminium trichloride, optionally in an inert solvent such as an aromatic solvent, at a temperature of between 20° C. and the boiling temperature of the reaction mixture.

The derivatives of formula (XIII) can be prepared by application or adaptation of the method described by T. Shono et al., J. Am. Chem. Soc., 104, 6697 (1982).

The derivatives of formula (XI) in which $R_2$ denotes an alkoxycarbonyl, cycloalkoxycarbonyl or cycloalkylalkoxycarbonyl radical and Z denotes a tert-butyl radical can be prepared by esterification of an acid of formula:

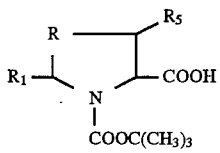

in which R denotes a methylene, ethylene, CHOH or $CHR_6$ radical or a sulphur atom, and $R_1$, $R_5$ and $R_6$ have the same meanings as in formula (I).

This esterification is performed in the conditions described above for the esterification of the acids of formula (VI) or by means of an alcohol in the presence of tosyl chloride, in pyridine.

The acids of formula (XIV) can be obtained by the action of di-tert-butyl dicarbonate on an acid of formula (VI).

This action is performed in an inert solvent such as water, dioxane or a mixture of these solvents, in the presence of an alkali metal carbonate, at a temperature close to 20° C.

The derivatives of formula (XI) in which $R_2$ denotes a residue-$CONR_9R_{10}$ and Z denotes a tert-butyl radical can be obtained by reaction of an acid of formula (XIV) or a reactive derivative of this acid with an amine of formula:

$$HNR_9R_{10} \quad (XV)$$

in which $R_9$ and $R_{10}$ have the same meanings as in formula (I).

When the acid is used, the operation is performed in the presence of a condensing agent employed in peptide chemistry, such as a carbodiimide (for example N,N'-dicyclohexylcarbodiimide) or N,N'-diimidazolecarbonyl, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the reflux temperature of the reaction mixture.

When a reactive derivative of the acid is used it is possible to react the anhydride, a mixed anhydride or an ester (which may be chosen from the activated or unactivated esters of the acid).

The operation is then carried out in an organic medium, optionally in the presence of an acid-scavenger such as a nitrogenous organic base (for example trialkylamine, pyridine, 1,8-diazabicyclo[5.4.0]undec-7-ene or 1,5-diazabicyclo[4.3.0]non-5-ene), in a solvent such as mentioned above or a mixture of these solvents, at a temperature of between 0° C. and the reflux temperature of the reaction mixture, or in a two-phase hydroorganic medium in the presence of an alkaline or alkaline-earth base (sodium hydroxide, potassium hydroxide) or of a carbonate or bicarbonate of an alkali or alkaline-earth metal at a temperature of between 0° and 40° C.

The derivatives of formula (IV) in which R denotes a methylene radical, $R_1$ is defined as in the general formula (I) with the exception of the radicals where substituents may be altered during a reduction (for example a quinolyl radical or nitro substituent), $R_2$ denotes a phenyl radical optionally substituted by one or more radicals chosen from alkyl, alkoxy and hydroxyl radicals and $R_5$ denotes a hydrogen atom may be obtained by application or adaptation of the methods described by C. G. Overberger et al., J. Amer. Chem. Soc., 91, 887 (1969). This method involves reductions of pyrroles which can be obtained by application or adaptation of the methods described in Synthesis, 613 (1991), Tetrahedron Letters 4407–4410 (1986).

The derivatives of formula (IV) in which R denotes a methylene radical, $R_1$ denotes an optionally substituted pyridyl radical, optionally substituted quinolyl, optionally substituted naphthyl or phenyl optionally substituted by one or more substituents chosen from halogen atoms and alkyl, alkoxy, hydroxyl, amino, monoalkylamino, dialkylamino, alkoxycarbonyl, —CO—$NR_7R_8$ or —NH—CO—$CH_3$ radicals, $R_2$ denotes an alkoxycarbonyl, cycloalkoxycarbonyl or cycloalkylalkoxycarbonyl radical, and $R_5$ denotes a hydrogen atom can also be obtained by reduction of a derivative of formula:

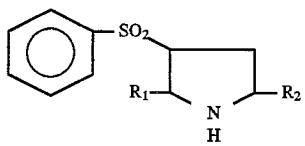

in which $R_1$ and $R_2$ have the same meanings as above.

This reduction is generally performed by means of a mercury-sodium amalgam, in the presence of sodium dihydrogenphosphate or sodium hydrogenphosphate in a solvent such as an alcohol (for example methanol), tetrahydrofuran, water or a mixture of these solvents, at a temperature of between −10° and 40° C., or by means of magnesium in an inert solvent such as an alcohol (for example methanol) at a temperature of between 20° C. and the boiling temperature of the reaction mixture.

The derivatives of formula (XVI) can be obtained by the action of a derivative of formula:

$$R_1—CH=N—CH_2—R_2 \quad (XVII)$$

in which $R_1$ and $R_2$ have the same meanings as above, on phenyl vinyl sulphone.

This reaction is generally performed in the presence of a metal salt such as lithium bromide or silver acetate and of a trialkylamine such as triethylamine, in an inert solvent such as acetonitrile, at a temperature close to 20° C.

The derivatives of formula (XVII) can be obtained by the action of an aldehyde of formula (VIII) in which $R_1$ has the same meanings as above, on an amine of formula:

$$R_2—CH_2—NH_2 \quad (XVIII)$$

in which $R_2$ has the same meanings as above.

This reaction is generally performed in an inert solvent such as a hydrocarbon (for example benzene, toluene), a chlorinated solvent (for example dichloromethane, chloroform), optionally in the presence of p-toluenesulphonic acid, at the boiling temperature of the reaction mixture.

The derivatives of formula (IV) in which R denotes a methylene radical, $R_1$ denotes a phenyl radical optionally substituted by one or more radicals chosen from alkylsubstoxy and hydroxyl or optionally substituted naphthyl radicals and $R_2$ denotes a phenyl radical optionally substituted by one or more radicals chosen from alkyl, alkoxy and hydroxyl radicals and $R_5$ denotes a hydrogen atom can also be obtained by reaction of ethylene with a derivative of formula (XVII) in which $R_1$ and $R_2$ have the same meanings as above.

The ethylene may be formed in situ by decomposition of tetrahydrofuran in the presence of a base such as butyllithium, at a temperature of between 0° and 25° C. It is also possible to add ethylene, in the presence of lithium diisopropylamide, in tetrahydrofuran, at a temperature close to 20° C.

The compounds of formula (IV) in which R denotes a methylene radical or CHOH, $R_1$ denotes a pyridyl, naphthyl, quinolyl or phenyl radical, $R_2$ denotes an alkoxycarbonyl, cycloalkoxycarbonyl, cyclalkylalkoxycarbonyl or phenyl radical optionally substituted by one or more substituents chosen from alkyl, alkoxy or hydroxyl radicals and $R_5$ denotes a hydrogen atom can be obtained by reduction of a derivative of formula:

(XIX)

in which R, $R_1$ and $R_2$ have the same meanings as above.

This reduction is preferably performed by means of hydrogen in the presence of a catalyst such as platinum oxide, in an inert solvent such as ethanol, at a temperature close to 20° C., or by means of sodium borohydride and potassium carbonate in a water-alcohol (preferably ethanol) mixture, at a temperature of between 0° and 20° C.

The derivatives of formula (XIX) can be obtained by application or adaptation of the methods described by A. Mkairi and J. Hamelin, Tetrahedron Letters, 28, 1397 (1987), A. van der Werf and R. M. Kellogg, Tetrahedron Letters, 32, 3727 (1991), E. Kato et al., Chem. Pharm. Bull., 33, 4836 (1985) and J. Ackermann et al., Helv. Chim. Acta, 73, 122 (1990).

The derivatives of formula (XIX) can also be obtained by deprotection and dehydration of a derivative of formula:

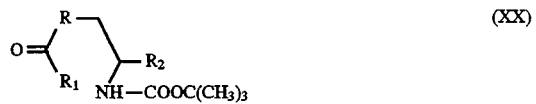

(XX)

or

(XXI)

in which R, $R_1$ and $R_2$ have the same meanings as above, or of a mixture of these derivatives.

The deprotection and dehydration are generally performed by means of trifluoroacetic acid or iodotrimethylsilane in an inert solvent such as a chlorinated solvent (for example dichloromethane) at a temperature close to 20° C.

The derivatives of formula (XX) and (XXI) can be obtained by the action of a derivative of formula:

$R_1$-M (XXII)

in which $R_1$ has the same meanings as above and $R_1$-M denotes an organomagnesium or organolithium derivative or a cuprate, on a carbonyl derivative of formula:

(XXIII)

in which R and $R_2$ have the same meanings as above.

This reaction is performed in an inert solvent such as tetrahydrofuran at a temperature of between −78° and 20° C.

The derivatives of formula (XXIII) can be obtained by application or adaptation of the methods described by J. Ackermann et al., Helv. Chim. Acta, 73, 122 (1990), T. Ohta et al., Chem. Lett., 2091 (1987) or T. Ohta et al., Tetrahedron Letters, 29, 329 (1988). Di-tert-butyl dicarbonate is preferably reacted with a derivative of formula:

(XXIV)

in which R and $R_2$ have the same meanings as above.

This reaction is generally performed in the presence of triethylamine and of 4-dimethylaminopyridine in a chlorinated solvent such as dichloromethane, at a temperature close to 20° C.

The derivatives of formula (XXIV) can be obtained by application or adaptation of the methods described by T. Kolasa et al., J. Org. Chem., 55, 1711 (1990), A. L. Johnson et al., J. Med. Chem., 28, 1596 (1985) and B. Rigo et al., J. Het. Chem., 25, 49 (1988), R. W. Rosemund and P. Engels, Arch. Pharm., 284, 16 (1951), C. F. Koelsch and C. H. Stratton, J. Am. Chem. Soc., 66, 1883 (1944), S. Widequist, Ark. Kemi, Mineral. Geol., 26, 1 (1948), J. Sinnreich and D. Elad, Tetrahedron Letters, 24, 4509 (1968), G. R. Brown et al., J. Chem. Soc., Chem. Commun., 1973 (1984).

The derivatives of formula (IV) in which R denotes a sulphur atom, $R_1$ is defined as in formula (I), $R_2$ denotes a phenyl radical optionally substituted by one or more substituents chosen from alkyl, alkoxy and hydroxyl radicals and $R_5$ denotes a hydrogen atom can be obtained by the action of a derivative of formula (VIII) on a 2-amino-2-phenylethanethiol in which the phenyl nucleus is optionally substituted by one or more substituents chosen from alkyl, alkoxy and hydroxyl radicals.

This reaction is generally performed in an inert solvent such as an alcohol, at the boiling temperature of the reaction mixture.

2-Amino-2-phenylethanethiols in which the phenyl nucleus is optionally substituted can be prepared by application or adaptation of the method described in Patent JP 57 197 447 which makes use of 2-amino-2-phenylethanols which are prepared by application or adaptation of the methods described by Z. L. Kis and J. Morly, EP 258 191, J. Pless, CH 590,820, S. Miyamoto et al., EP 432 661 and J. Suzuki et al., EP 345 775.

The derivatives of formula (IV) in which $R_2$ denotes a phenyl optionally substituted by one or more substituents chosen from alkyl, alkoxy or hydroxyl radicals, R denotes a methylene radical, $R_1$ denotes a hydrogen atom and $R_5$ denotes a phenyl radical can be prepared by application or adaptation of the methods described by W. H. Pearson et al., J. Am. Chem. Soc., 114, 1329 (1992), O. Tsuge et al., Bull. Chem. Soc. Japan, 59, 2537 (1986).

These derivatives can also be prepared by reduction of the corresponding pyrroles and pyrrolines by application or adaptation of the methods described by C. G. Overberger et al., J. Am. Chem. Soc., 91, 687 (1969).

These pyrroles and these pyrrolines can be prepared by application or adaptation of the methods described by M. Ohno et al., Tetrahedron Letters, 32, 5093 (1991), S. C. Cherkofsky, U.S. Pat. No. 4,267,184, S. C. Cherkofsky and G. A. Boswell Jr., EP 25884 and O. Tsuge et al., Bull. Chem. Soc. Japan, 59, 1809 (1986).

The derivatives of formula (IV) in which R denotes an ethylene radical, $R_2$ denotes a phenyl optionally substituted by one or more substituents chosen from alkyl, alkoxy or hydroxyl radicals, $R_5$ denotes a hydrogen atom and $R_1$ has the same meanings as in formula (I) can be prepared by application or adaptation of the methods described by C. G. Overberger et al., J. Am Chem. Soc., 79, 6430 (1957), J. Thesing and H. Meyer, Ann., 609, 46 (1957), D. Y. Jackson and P. G. Schultz, J. Am. Chem. Soc., 113, 2319 (1991) and C. G. Overberger and L. P. Herin, J. Org. Chem., 27, 2423 (1962).

Some of these methods make use of reductions of tetrahydropyridines which can also be obtained by application or adaptation of the methods described by H. Quast and B. Mueller, Chem. Ber., 116, 3931 (1983), R. Weil and N. Collignon, C. Rend. Acad. Sci. Ser. C, 275, 299 (1972) and Bull. Soc. Chim. Fr., 258 (1974).

The derivatives of formula (IV) in which $R_2$ denotes a phenyl optionally substituted by one or more substituents chosen from alkyl, alkoxy or hydroxyl radicals, R denotes a radical $CHR_6$, each of $R_1$ and $R_5$ denotes a hydrogen atom and $R_6$ denotes a phenyl radical can be prepared by application or adaptation of the methods described by M. C. Kloezel, J. Am. Chem. Soc., 69, 2271 (1947), W. H. Pearson et al., J. Am. Chem. Soc., 114, 1329 (1992), O. Tsuge et al., Bull. Soc. Japan, 59, 2537 (1986), M. Carriou et al., Can. J. Chem., 61, 2359 (1983) and E. Brewer and D. Melumad, J. Org. Chem., 37, 3949 (1972).

Some of these methods make use of reductions of pyrroles and of pyrrolines which can also be obtained by application or adaptation of the methods described by C. F. H. Allen and C. V. Wilson, Org. Synth. Coll. Vol. III, 358 (1955), W. Davey and D. J. Tivey, J. Chem. Soc., 2276, (1958), W. Chen et al., Chin. Chem. Lett., 2, 439 (1991) and S. M. Bloom and P. P. Garcia, U.S. Pat. No. 3,883,555 and U.S. Pat. No. 3,691,161.

The derivatives of formula (III) in which $R_2$ denotes an alkoxycarbonyl, cycloalkoxycarbonyl or cycloalkylalkoxycarbonyl radical can also be obtained by esterification of an acid of formula:

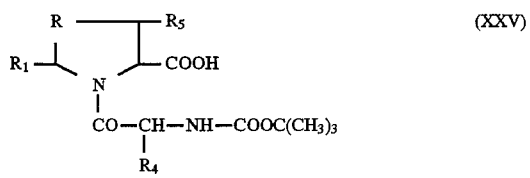

(XXV)

in which R, $R_1$, $R_4$, $R_5$ and $R_6$ have the same meanings as in formula (I).

This reaction is preferably performed in the same conditions as those described above for the esterification of the compounds of formula (XIV).

The acids of formula (XXV) can be obtained by hydrolysis of the corresponding methyl or ethyl esters of formula (III).

This hydrolysis is generally performed in an inert solvent such as water, dioxane or a mixture of these solvents, by means of a base such as an alkali metal hydroxide (sodium hydroxide, potassium hydroxide) at a temperature close to 20° C.

The derivatives of formula (III) in which R denotes a methylene radical, $R_1$ denotes an optionally substituted pyridyl radical, optionally substituted quinolyl, optionally substituted naphthyl or phenyl optionally substituted by one or more substituents chosen from halogen atoms and alkyl, alkoxy, hydroxyl, amino, monoalkylamino, dialkylamino, alkoxycarbonyl, —CO—$NR_7R_8$ or —NH—CO—$CH_3$ radicals, $R_2$ denotes an alkoxycarbonyl, cycloalkoxycarbonyl or cycloalkylalkoxycarbonyl radical and $R_5$ denotes a hydrogen atom can be obtained by reduction of the derivatives of formula:

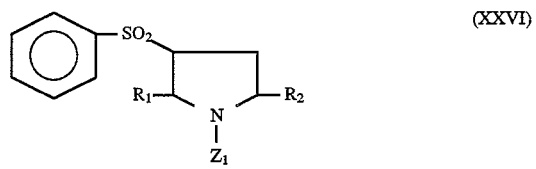

(XXVI)

in which $Z_1$ denotes a radical —CO—$CH(R_4)$—NH—$COOC(CH_3)_3$, $R_1$ and $R_2$ have the same meanings as above and $R_4$ has the same meanings as in formula (I).

This reaction is performed in the same conditions as those described above for the reduction of the derivatives of formula (XVI).

The derivatives of formula (XXVI) can be obtained by the action of an acid of formula (V) on a derivative of formula (XVI).

This reaction is performed in an inert solvent such as acetonitrile, tetrahydrofuran or a chlorinated solvent, in the presence of a condensing agent employed in peptide chemistry, such as a carbodiimide (for example N,N'-dicyclohexylcarbodiimide) or an alkyl chloroformate, at a temperature of between 10° and 40° C.

The derivatives of formula (XI) in which R denotes a methylene radical and Z denotes a tert-butyl radical can be obtained by reduction of the derivatives of formula:

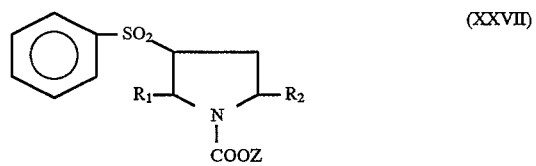

(XXVII)

in which $R_1$ and $R_2$ have the same meanings as in formula (I) and Z denotes a tert-butyl radical.

This reduction is performed in the same conditions as those described above for the reduction of derivatives of formula (XVI).

The derivatives of formula (XXVII) can be obtained by the action of a derivative of formula (XVI) with di-tert-butyl dicarbonate.

This reaction is performed in an inert solvent such as a chlorinated solvent (for example dichloromethane), in the presence of an organic base such as a trialkylamine (for example triethylamine) or of an alkali metal carbonate or bicarbonate, at a temperature close to 20° C.

Optionally substituted anilines are available commercially or can be obtained by application or adaptation of the methods described by R. Schröter, Methoden der organischen Chemie, Houben Weil, volume XI/1, p 360; G. J. Esselen et al., J. Am. Chem. Soc., 36, 322 (1914); G. Adriant et al., Bull. Soc. Chim. FR, 1511 (1970); W. A. Jacobs et al., J. Am. Chem. Soc., 39, 2438 (1917) and J. Am. Chem. Soc., 39, 1438 (1917) and in the examples.

The compounds of formula (I) in which $R_3$ denotes a phenylamino radical in which the phenyl nucleus is substituted by a carboxyl, -alk-COOH, —O-alk-COOH, -alk'-COOH, —CH=CH—COOH, —CO—COOH, —S-alk-COOH, —SO-alk-COOH, —SO$_2$-alk-COOH, —C(=NOH)—COOH, —O—CH$_2$-alk'-COOH or —CX=N—O-alk-COOH radical and $R_1$, $R_2$, $R_5$ and $R_6$ are defined as in formula (I) can also be prepared by hydrolysis or, depending on the case, hydrogenolysis of the corresponding esters of formula (I).

When the alkyl or phenylalkyl esters are employed, it is advantageous to perform the hydrolysis by means of a base such as sodium hydroxide, potassium hydroxide or lithium hydroxide, in an inert solvent such as tetrahydrofuran, dioxane, water or a mixture of these solvents, at a temperature of between 20° C. and 40° C. When a trimethylsilylethyl ester is employed, it is advantageous to operate in an inert solvent such as tetrahydrofuran, by means of a fluoride such as tetrabutylamunonium fluoride, at a temperature of between 10° and 40° C. When phenylalkyl esters are employed, it is perhaps also advantageous to perform a hydrogenolysis by means of hydrogen or else ammonium formate in the presence of a catalyst such as palladium on charcoal in a solvent such as methanol or ethyl acetate.

The trimethylsilylethyl esters can be obtained by application or adaptation of the method described by H. Gerlach, Helv. Chim. Acta, 60, 3039 (1977).

The compounds of formula (I) in which $R_3$ denotes a phenylamino radical in which the phenyl nucleus is optionally substituted by a hydroxyiminoalkyl or alkoxyiminoalkyl radical can also be prepared by the action of the corresponding acylated derivative of formula (I) on a derivative of formula:

$$H_2N—OR_{17} \qquad (XXVIII)$$

in which $R_{17}$ denotes a hydrogen atom or an alkyl radical.

This reaction is generally performed in an inert solvent such as an alcohol (for example methanol or ethanol), water or a mixture of these solvents, at the boiling temperature of the solvent and optionally in the presence of a base such as pyridine.

The compounds of formula (I) in which R denotes an SO or SO$_2$ radical, $R_1$, $R_2$ and $R_5$ are defined as in the general formula (I) can be prepared by oxidation of the corresponding compounds of formula (I) in which R denotes a sulphur atom, it being understood that the other radicals and the other substituents are chosen so that they are insensitive to the reaction conditions.

This oxidation is generally performed by means of oxone® (potassium peroxymonosulphate) marketed by Aldrich, in an alcohol such as methanol or a methanol-water mixture, at a temperature close to 25° C.

A person skilled in the art understands that, to make use of the processes according to the invention which are described above, it may be necessary, in order to avoid secondary reactions, to introduce protective groups for the amine, alcohol, acid and ketone functional groups, such as those described by T. W. Greene, Protective groups in organic synthesis, John Wiley and Sons, New York. For example, the amine functional groups can be blocked in the form of tert-butyl or methyl carbamates and then regenerated with iodotrimethylsilane, or in the form of benzyl carbamates and then regenerated by hydrogenation after the process according to the invention has been used. The alcohol functional groups may, for example, be blocked in the form of benzoate and then regenerated by hydrolysis in alkaline medium after the process according to the invention has been used.

The enantiomers of the compounds of formula (I) containing at least one asymmetric site can be obtained by resolving the racemates, for example by chromatography on a chiral column or by synthesis from chiral precursors.

The chiral phase employed is preferably a phase in which the chiral selector which is, preferably, 3,5-dinitrobenzoyl-D-phenylglycine is kept at a distance from the silica by an aminoalkanoyl arm containing 3 to 14 carbon atoms, bound to the amine functional groups of an aminopropylsilica and in which the free silanol functional groups are blocked by trialkylsilyl radicals.

This chiral phase can be defined by the following structure:

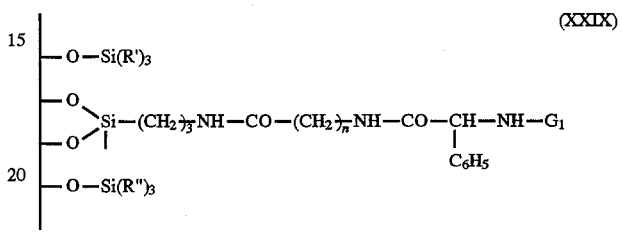

(XXIX)

in which the symbols R', which are identical or different, and R" which are identical or different, denote alkyl radicals containing 1 to 10 carbon atoms, $G_1$ denotes an electron-withdrawing group and n denotes an integer from 3 to 13 inclusive.

One of the symbols R' preferably denotes an alkyl radical containing 7 to 10 carbon atoms, and the other two denote an alkyl radical containing 1 to 2 carbon atoms and preferably a methyl radical, the symbols R" are identical and denote a methyl or ethyl radical, $G_1$ denotes a benzoyl radical optionally substituted, preferably, by one or more nitro radicals, such as the 3,5-dinitrobenzoyl radical, and n is equal to 10.

The chiral phase can be prepared by the action on an aminopropylsilica of the anhydride of an aminoalkanoic acid containing 3 to 14 carbon atoms in which the amine functional group is protected by a protective group such as the tert-butoxycarbonyl radical, followed by the blocking of a proportion of the silanol functional groups using Si(R')$_3$ radicals such as defined above and then, after removal of the protective group from the amine functional group, by the amidification by means of D-phenylglycine whose amine functional group is protected by an electron-withdrawing group $G_1$ as defined above and, finally, the blocking of the residual silanol functional groups using Si(R")$_3$ radicals as defined above.

The action of the anhydride of a protected aminoalkanoic acid on the aminopropylsilica is generally performed by operating in an anhydrous organic solvent such as dimethylformamide at a temperature close to 20° C.

The blocking of the silanol functional groups using —Si (R$_3$) groups as defined above is performed by the action of a halotrialkylsilane on the aminopropylsilica grafted using aminoalkanoyl residues, the operation being performed in an organic solvent such as methylene chloride in the presence of a basic agent such as pyridine.

When the protective group is a tert-butoxycarbonyl radical, the removal of the protective groups from the aminoalkanoyl residues is generally performed by the action of trifluoroacetic acid in an organic solvent such as methylene chloride.

The amidification by means of D-phenylglycine whose amine functional group is protected is performed in the presence of a condensing agent such as N-ethoxycarbonyl-2-ethoxy-1,2-dihydroquinoline, the operation being carried out in an anhydrous organic solvent such as dimethylformamide.

The blocking of the residual silanol functional groups using —Si(R")$_3$ radicals as defined above is generally performed by means of trialkylsilylimidazole, the operation being carried out in an organic solvent such as methylene chloride.

The compounds of formula (I) can be purified by the usual known methods, for example by crystallization, chromatography or extractions.

The compounds of formula (I) containing a basic residue can be optionally converted into addition salts with an inorganic or organic acid by the action of such an acid in an organic solvent such as an alcohol, a ketone, an ether or a chlorinated solvent.

The compounds of formula (I) containing an acidic residue can optionally be converted into metal salts or into addition salts with nitrogenous bases, by methods which are known per se. These salts can be obtained by the action of a metallic base (for example of an alkali or alkaline-earth metal), of ammonia, of an amine or of a salt of an amine on a compound of formula (I), in a solvent. The salt formed is isolated by the usual methods.

These salts also form part of the invention.

Examples of pharmaceutically acceptable salts which may be mentioned are the addition salts with inorganic or organic acids (such as the acetate, propionate, succinate, benzoate, fumarate, maleate, oxalate, methanesulphonate, isethionate, theophyllinacetate, salicylate, methylene-bis-β-oxynaphthoate, hydrochloride, sulphate, nitrate and phosphate), salts with alkali metals (sodium, potassium, lithium) or with alkaline-earth metals (calcium, magnesium), the ammonium salt, the salts of nitrogenous bases (ethanolamine, trimethylamine, methylamine, benzylamine, N-benzyl-β-phenethylamine, choline, arginine, leucine, lysine or N-methylglucamine).

The compounds of formula (I) exhibit advantageous pharmacological properties. These compounds have a high affinity for the cholecystokinin (CCK) and gastrin receptors and are therefore useful in the treatment and the prevention of the disorders related to CCK and to gastrin affecting the nervous system and the gastrointestinal apparatus.

These compounds can thus be employed for the treatment or the prevention of psychoses, of anxious disorders, of depression, of neurodegeneration, of panic attacks, of Parkinson's disease, of tardive dyskinesia, of the irritable colon syndrome, of acute pancreatitis, of ulcers, of intestinal motility disorders, of certain CCK-sensitive tumours, as appetite regulator, in the withdrawal of chronic treatments and abuse of alcohol or of medications and as constrictor of the pupil of the eye.

These compounds also have a potentializing effect on the analgesic activity of narcotic and nonnarcotic medications. In addition, they may have a specific analgesic effect.

Furthermore, the compounds which have a high affinity for the CCK receptors modify the memorizing abilities. Consequently, these compounds may be efficacious in memory disturbances.

The affinity of the compounds of formula (I) for the CCK receptors has been determined by a technique inspired by that of A. Saito et al., (J. Neuro. Chem., 37, 483–490 (1981)) relating to the cerebral cortex and the pancreas.

In these tests the IC$_{50}$ of the compounds of formula (I) is generally lower than or equal to 1000 nM.

Furthermore, it is known that the products which recognize the central CCK receptors have a similar specificity for the gastrin receptors in the gastrointestinal tract (Bock et al., J. Med. Chem., 32, 16–23 (1989); Reyfeld et al., Am. J. Physiol., 240, G255–266 (1981); Beinfeld et al., Neuropeptides, 3, 411–427 (1983).

The compounds of formula (I) exhibit a low toxicity. Their LD$_{50}$ is generally higher than 40 mg/kg by subcutaneous route in the mouse.

EXAMPLE

The following example illustrates the invention without limiting it.

Example 1

A solution of 1.6 g of (2R,4R)-tert-butyl{3-[2-(1-imidazolylcarboxamido)acetyl]-2-(2-fluorophenyl) thiazolidine-4-carboxylate and of 1.4 g of sodium 3-aminophenylmethanesulphinate in 55 cm3 of a toluene-dimethylformamide mixture (90/10 by volume) is heated to reflux for 4 hours. After returning to a temperature close to 25° C. the reaction mixture is diluted with 20 cm3 of a 0.5N aqueous solution of hydrochloric acid and extracted with 2 times 50 cm3 of ethyl acetate. The combined organic phases are washed with 50 cm3 of water and then extracted with 2 times 10 cm3 of a 1N aqueous solution of sodium hydroxide. The basic aqueous phases are combined, brought to a pH close to 1 by adding a 1N aqueous solution of sulphuric acid and extracted with 2 times 25 cm3 of ethyl acetate. The combined organic phases are washed with 25 cm3 of water, are dried over magnesium sulphate and are concentrated to dryness at reduced pressure at 40° C. 0.03 g of (2R,4R)-3-{3-{2-[4-tert-butoxycarbonyl-2-(2-fluorophenyl)-3-thiazolidinyl]-2-oxoethyl}ureido}phenylmethanesulphinic acid are thus obtained in the form of an amorphous product.

NMR (δ ppm, DMSO-D$_6$+2 drops of CD$_3$COOD, 393K): 1.50 (s, 9H, CO$_2$tBu), 3.20 to 3.60 (mt, 2H, —S—CH$_2$—), 3.85 (s, 2H, Ar—CH$_2$—SO$_2$—), 3.70 to 4.20 (mt, 2H, N—CH$_2$—CO—), 5.00 (mt, 1H, N—CH—CO—), 6.53 (s, 1H, N—CH—S—), 6.80 to 8.00 (mt, 8H, aromatics).

A. (2R,4R)-tert-Butyl{3-[2-(1-imidazolylcarboxamido) acetyl]-2-(2-fluorophenyl)thiazolidine-4-carboxylate can be prepared in the following manner: a solution of 4.8 g of N,N'-diimidazolecarbonyl in 50 cm3 of anhydrous tetrahydrofuran is added slowly at a temperature close to 25° C. to a solution of 7.0 g of (2R,4R)-tert-butyl 3-(2-aminoacetyl)-2-(2-fluorophenyl)thiazolidine-4-carboxylate in 100 cm3 of anhydrous tetrahydrofuran. The reaction mixture is stirred for 12 hours at a temperature close to 25° C. and then concentrated to dryness at reduced pressure at 35° C. The residue obtained is dissolved in 200 cm3 of ethyl acetate and washed with 2 times 50 cm3 of water. The organic phase is dried over magnesium sulphate and evaporated to dryness at reduced pressure at 40° C. 8.7 g of (2R,4R)-tert-butyl{3-[2-(1-imidazolylcarboxamido)acetyl]-2-(2-fluorophenyl) thiazolidine-4-carboxylate are thus obtained in the form of a yellow oil, employed as it is in the subsequent syntheses.

B. (2R,4R)-tert-Butyl 3-(2-aminoacetyl)-2-(2-fluorophenyl)thiazolidine-4-carboxylate can be prepared in the following manner: 5.4 cm3 of iodotrimethylsilane are added dropwise at a temperature close to 25° C. to a solution of 15.0 g of (2R,4R)-tert-butyl 3-(2-tert-butoxycarbonylaminoacetyl)-2-(2-fluorophenyl)-thiazolidine-4-carboxylate in 150 cm3 of chloroform. The reaction mixture is stirred for 3 hours at a temperature close to 25° C. and 50 cm3 of water are then added. After density separation the aqueous phase is separated off and extracted with 2 times 50 cm3 of chloroform. The combined organic phases are washed successively with 50 cm3 of water, 50 cm3 of a saturated aqueous solution of sodium hydrogencarbonate and 50 cm3 of a saturated aqueous solution of sodium chloride, and are then dried over magnesium sulphate and concentrated to dryness at reduced pressure at 40° C. 10.0 g of (2R,4R) tert-butyl 3-(2-aminoacetyl)-2-(2-fluorophenyl) thiazolidine-4-carboxylate are thus obtained in the form of a yellow oil which is employed as it is in the subsequent syntheses.

C. (2R,4R)-tert-Butyl 3-(2-tert-butoxycarbonylamino)-2-(2-fluorophenyl)-thiazolidine-4-carboxylate can be prepared in the following manner: a solution of 18.2 g of N,N'-dicyclohexylcarbodiimide in 75 cm3 of anhydrous acetonitrile is added over 30 minutes to a solution of 25.0 g of (2RS,4R)-tert-butyl 2-(2-fluorophenyl)thiazolidine-4-carboxylate and of 15.5 g of 2-tert-butoxycarbonylaminoacetic acid in 150 cm3 of anhydrous acetonitrile, maintained at a temperature close to 0° C. The reaction mixture is stirred for 16 hours at a temperature close to 25° C. The insoluble product is separated off by filtration, washed with 3 times 20 cm3 of acetonitrile, and the filtrate is concentrated to dryness at reduced pressure at 40° C. The crude product obtained is purified by chromatography on silica [eluent: ethyl acetatecyclohexane (30–70 by volume)]. The fractions containing the expected product are combined and concentrated to dryness at reduced pressure at 40° C. 25.0 g of (2R,4R)-tert-butyl 3-(2-tert-butoxycarbonylaminoacetyl)-2-(2-fluorophenyl)thiazolidine-4-carboxylate are thus obtained in the form of an oil, which is employed as it is in the subsequent syntheses.

D. (2RS,4R)-tert-Butyl 2-(2-fluorophenyl)thiazolidine-4-carboxylate can be prepared in the following manner: 1.5 cm3 of concentrated sulphuric acid are added dropwise to a suspension, cooled to a temperature close to 5° C., of 5.7 g of (2RS,4R)-2-(2-fluorophenyl)-thiazolidine-4-carboxylic acid in 60 cm3 of chloroform. The reaction mixture is saturated with isobutene for 3 hours while the temperature of the reaction mixture is maintained in the vicinity of 5° C. After returning to a temperature close to 25° C. stirring is continued for 12 hours. The reaction mixture is treated with 50 cm3 of a saturated aqueous solution of sodium hydrogencarbonate. The organic phase is separated off and the aqueous phase is extracted with 2 times 40 cm3 of chloroform. The combined organic phases are washed with 50 cm3 of water and with 50 cm3 of a saturated aqueous solution of sodium chloride, are dried over magnesium sulphate and are concentrated to dryness at reduced pressure at 40° C. 5.8 g of (2RS,4R)-tert-butyl 2-(2-fluorophenyl)-thiazolidine-4-carboxylate are thus obtained in the form of a yellow oil, employed as it is in the subsequent syntheses.

E. (2RS,4R)-2-(2-Fluorophenyl)thiazolidine-4-carboxylic acid can be prepared in the following manner: 22.7 g of 2-fluorobenzaldehyde are added at a temperature close to 50° C. to a suspension of 21.2 g of L-cysteine in 150 cm3 of ethanol. The reaction mixture is heated to reflux for 3 hours. After cooling to a temperature close to 25° C. the insoluble product is separated off by filtration and washed with 2 times 50 cm3 of ethanol and 2 times 50 cm3 of diethyl ether. 28.2 g of (2RS,4R)-2-(2-fluorophenyl)thiazolidine-4-carboxylic acid, melting at 147° C, are thus obtained.

F. Sodium 3-aminophenylmethanesulphinate can be prepared in the following manner: a solution of 7 g of sodium 3-nitrophenylmethanesulphinate in 1000 cm3 of ethanol and 10.0 g of Raney nickel are introduced in succession into a single-necked flask purged with nitrogen. The suspension is stirred for 1 hour under hydrogen atmosphere (100 kPa) at a temperature close to 25° C. and charcoal is then added and the catalyst is separated off by filtration. The filtrate is concentrated to dryness at reduced pressure at 40° C. 6.0 g of sodium 3-aminophenylmethanesulphinate are thus obtained in the form of a hygroscopic white solid form, employed as it is in the subsequent syntheses.

G. Sodium 3-nitrophenylmethanesulphinate can be prepared in the following manner: 3.8 g of sodium borohydride are added to a suspension of 16.6 g of 2-[(3-nitrophenyl)methylsulphonyl)benzothiazole in 400 cm3 of an ethanol-tetrahydrofuran mixture (10/90 by volume). The reaction mixture is stirred for 16 hours at a temperature close to 25° C. The insoluble material is separated off by filtration and washed with 2 times 50 cm3 of ethanol. 9.2 g of sodium 3-nitrophenylmethanesulphinate are thus obtained in the form of a yellow powder, which is employed as it is in the subsequent syntheses.

H. 2-[(3-Nitrophenyl)methylsulphonyl]benzothiazole can be prepared in the following manner: a solution of 12.6 g of potassium permanganate in 750 cm3 of water is added over 45 minutes to a solution of 20.0 g of 2-[(3-nitrophenyl)methylthio]benzothiazole in 1000 cm3 of acetic acid. The reaction mixture is stirred for 18 hours at a temperature close to 25° C. and an aqueous solution of 6.5 g of sodium sulphite in 50 cm3 of water is then added dropwise. The solid thus precipitated is separated off by filtration and washed with 20 cm3 of ethanol and 30 cm3 of diethyl ether. 19.2 g of 2-[(3-nitrophenyl)methylsulphonyl]benzothiazole are thus obtained in the form of a white powder melting at 168° C.

I. 2-[(3-Nitrophenyl)methylthio]benzothiazole can be prepared in the following manner: 150 cm3 of a 1N aqueous solution of sodiumhydroxide are added to a suspension of 25.9 g of 2-mercaptobenzothiazole in 500 cm3 of methanol, followed by 25.0 g of 3-nitrophenylmethyl chloride. The reaction mixture is stirred for 18 hours at a temperature close to 25° C. and then concentrated to dryness at reduced pressure at 40° C. The residue obtained is taken up in 500 cm3 of water and extracted with 4 times 250 cm3 of dichloromethane. The combined organic phases are dried over magnesium sulphate and concentrated to dryness at reduced pressure. 39.3 g of 2-[(3-nitrophenyl)methylthio]benzothiazole are thus obtained in the form of a yellow powder melting at 160° C.

The medications according to the invention consist of a compound of formula (I) in free form or in the form of a salt, in the pure state or in the form of a composition in which it is used in combination with any other pharmaceutically compatible product, which may be inert or physiologically active. The medications according to the invention can be employed by an oral, parenteral, rectal or topical route.

Tablets, pills, powders (gelatin capsules, cachets) or granules may be employed as solid compositions for oral administration. In these compositions the active principle according to the invention is mixed with one or a number of inert diluents such as starch, cellulose, sucrose, lactose or silica, under a stream of argon. These compositions may also include substances other than diluents, for example one or more lubricants such as magnesium stearate or talc, a colorant, a coating (sugar-coated pills) or a varnish.

Pharmaceutically acceptable solutions, suspensions, emulsions, syrups and elixirs containing inert diluents such as water, ethanol, glycerol, vegetable oils or liquid paraffin may be employed as liquid compositions for oral administration. These compositions may include substances other than the diluents, for example wetting products, sweeteners, thickeners, flavors or stabilizers.

The sterile compositions for parenteral administration may be preferably aqueous or nonaqueous solutions, suspensions or emulsions. The solvent or carrier employed may be water, propylene glycol, a polyethylene glycol, vegetable oils, in particular olive oil, injectable organic esters, for example ethyl oleate, or other suitable organic solvents. These compositions may also contain adjuvants, in particular wetting and isotonicity agents, emulsifiers, dispersants and stabilizers. The sterilization may be carried out in a number of ways, for example by aseptic filtration, by incorporating sterilizing agents into the composition, by irradiation or by heating. They may also be prepared in the form of sterile solid compositions which can be dissolved at the time of use in sterile water or any other injectable sterile medium.

The compositions for rectal administration are suppositories or rectal capsules which, in addition to the active product, contain excipients such as cocoa butter, semisynthetic glycerides or polyethylene glycols.

The compositions for topical administration may be, for example, creams, lotions, eye lotions, mouthwashes, nasal drops or aerosols.

In human therapeutics the compounds according to the invention are particularly useful in the treatment and prevention of disorders related to CCK and gastrin affecting the nervous system and the gastrointestinal apparatus. These compounds can therefore be employed in the treatment and the prevention of psychoses, of anxious disorders, of depression, of neurodegeneration, of panic attacks, of Parkinson's disease, of tardive dyskinesia, of the irritable colon syndrome, of acute pancreatitis, of ulcers, of intestinal motility disorders, of certain CCK-sensitive tumours, of memory disorders, in the withdrawal of chronic treatments and abuse of alcohol or of medications, as constrictors of the pupil of the eye, as analgesics, as potentiators of the analgesic activity of narcotic and nonnarcotic analgesic medications and as appetite regulators.

The dosages depend on the effect sought after, on the duration of the treatment and on the administration route employed; they are generally between 0.05 g and 1 g daily orally in the case of an adult, with unit doses ranging from 10 mg to 500 mg of active substance.

In general, the medical practitioner will determine the appropriate posology as a function of the age, weight and all the other factors specific to the subject to be treated.

The following examples illustrate compositions according to the invention:

EXAMPLE A

Gelatin capsules containing 50-mg doses of active product, which have the following composition, are prepared by the usual technique:

| | |
|---|---|
| (2R,4R)-3-{3-{2-[4-tert-Butoxy-carbonyl-2-(2-fluorophenyl)-3-thiazolidinyl]-2-oxoethyl}ureido-phenylmethanesulphinic acid | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing a 50-mg dose of active product, which has the following composition, are prepared by the usual technique:

| | |
|---|---|
| (2R,4R)-3-{3-{2-[4-tert-Butoxy-carbonyl-2-(2-fluorophenyl)-3-thiazolidinyl]-2-oxoethyl}ureido-phenylmethanesulphinic acid | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethyl cellulose, glycerine, titanium oxide (72-3.5-24.5) q.s. 1 film-coated tablet finished at 245 mg | |

EXAMPLE C

An injectable solution containing 10 mg of active product which has the following composition is prepared:

| | |
|---|---|
| (2R,4R)-3-{3-{2-[4-tert-Butoxy-carbonyl-2-(2-fluorophenyl)-3-thiazolidinyl]-2-oxoethyl}ureido-phenylmethanesulphinic acid | 10 mg |
| Benzoic acid | 80 mg |
| Benzyl alcohol | 0.06 cm$^3$ |
| Sodium benzoate | 80 mg |
| 95% ethanol | 0.4 cm$^3$ |
| Sodium hydroxide | 24 mg |
| Propylene glycol | 1.6 cm$^3$ |
| Water q.s. | 4 cm3 |

Although the invention has been described in conjunction with specific embodiments, it is evident that many alternatives and variations will be apparent to those skilled in the art in light of the foregoing description. accordingly, the invention is intended to embrace all of the alternatives and variations that fall within the spirit and scope of the appended claims. The above references are hereby incorporated by reference.

We claim:

1. A compound of formula (I):

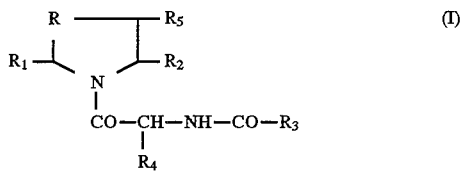

in which

R denotes a methylene, ethylene, SO, SO$_2$ or CHOH radical or a sulphur atom, R$_1$ denotes a pyridyl radical optionally substituted by at least one alkyl radical, a furyl radical optionally substituted by at least one alkyl radical, a thienyl radical optionally substituted by at least one alkyl radical, a quinolyl radical optionally substituted by at least one alkyl radical, a naphthyl radical optionally substituted by at least one alkyl radical, an indolyl radical optionally substituted by at least one alkyl radical, or a phenyl radical optionally substituted by at least one substituent selected from halogen atoms and alkyl, alkoxy, hydroxyl, nitro, amino, monoalkylamino, dialkylamino, alkoxycarbonyl, —CO—NR$_7$R$_8$, —NH—CO—CH$_3$, trifluoromethyl and trifluoromethoxy radicals, and R$_5$ denotes a hydrogen atom, or R denotes a methylene radical, $R_1$ denotes a hydrogen atom and $R_5$ denotes a phenyl radical, or R denotes a radical $CHR_6$, each of $R_1$ and $R_5$ denoting a hydrogen atom, $R_2$ denotes an alkoxycarbonyl, cycloalkoxycarbonyl, cycloalkylalkoxycarbonyl, —$CONR_9R_{10}$ or phenyl radical optionally substituted by at least one substituent selected from alkyl, alkoxy or hydroxyl radicals, $R_3$ denotes a phenylamino radical in which the phenyl nucleus is substituted by at least one substituent selected from the radicals -alk-$SO_2H$, —$SO_2$—NH—CO—$R_{11}$, —$B(OH)_2$, —$SO_2$—NH—$SO_2$—$R_{11}$, —CO—NH—CO—$R_{11}$, —CO—NH—$SO_2$—$R_{11}$, —C($NH_2$)=NOH, —$SO_2$NH—$R_{12}$, —CO—NH—$R_{12}$,

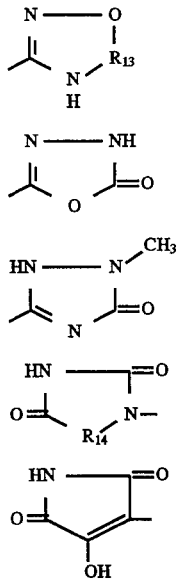

and optionally substituted by at least one substituent selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$ (in salt form), —CH=CH-alk', —C(=NOH)—COOX, —S-alk-COOX, —SO-alk-COOX, —$SO_2$-alk-COOX, —O—$CH_2$-alk'-COOX, —CX=N—O-alk-COOX, -alk-N(OH)—CO-alk and 2,2-dimethyl-4,6-dioxo-1,3-dioxan-5-yl radicals, $R_4$ denotes a hydrogen atom or an alkyl radical, $R_6$ denotes a phenyl radical, $R_7$ denotes a hydrogen atom or an alkyl, phenylalkyl or phenyl radical optionally substituted by at least one substituent selected from halogen atoms and alkyl, alkoxy and alkylthio radicals, $R_8$ denotes an alkyl, phenylalkyl or phenyl radical optionally substituted by at least one substituent selected from halogen atoms and alkyl, alkoxy and alkylthio radicals, or else $R_7$ and $R_8$ together with the nitrogen atom to which they are attached form a saturated or unsaturated mono- or polycyclic heterocyclic ring containing 4 to 9 carbon atoms and at least one heteroatom selected from O and N, and said heterocyclic ring optionally being substituted by at least one alkyl radical, $R_9$ denotes a hydrogen atom or an alkyl, cycloalkylalkyl, cycloalkyl, phenylalkyl or phenyl radical optionally substituted by at least one substituent selected from halogen atoms and alkyl, alkoxy and alkylthio radicals, $R_{10}$ denotes an alkyl, cycloalkylalkyl, cycloalkyl, phenylalkyl or phenyl radical optionally substituted by at least one substituent selected from halogen atoms and alkyl, alkoxy and alkylthio radicals, or else $R_9$ and $R_{10}$ together with the nitrogen atom to which they are attached form a saturated or unsaturated mono- or polycyclic heterocyclic ring containing 4 to 9 carbon atoms and at least one heteroatom selected from O, N, and S, and said heterocyclic ring optionally being substituted by at least one alkyl radical, $R_{11}$ denotes an alkyl, cycloalkyl, trifluoromethyl or phenyl radical optionally substituted by at least one substituent selected from cyano, alkoxy, nitro and amino radicals and halogen atoms, $R_{12}$ denotes a 5-tetrazolyl radical, $R_{13}$ denotes C=O or S=O, $R_{14}$ denotes O or C=O, X denotes a hydrogen atom or an alkyl or phenylalkyl radical, alk denotes an alkyl or alkylene radical, alk' denotes a hydroxyalkyl, hydroxyalkylene, alkoxyalkyl or alkoxyalkylene radical, wherein the alkyl, alkylene and alkoxy radicals and those radicals having alkyl, alkylene and alkoxy parts contain 1 to 4 carbon atoms as a straight or branched chain, the acyl radicals and those radicals having acyl parts contain 2 to 4 carbon atoms and the cycloalkyl radicals and those radicals having cycloalkyl parts contain 3 to 6 carbon atoms, or a salt of a compound of formula I or an isomer of a compound of formula I, when said compound contains at least one asymmetric center.

2. A compound of formula (I) according to claim 1, wherein $R_7$ and $R_8$ with the nitrogen atom to which they are attached form a heterocyclic ring selected from piperidino rings optionally substituted by at least one alkyl or 1,2,3,4-tetrahydroquinoline radical.

3. A compound of formula (I) according to claim 1, wherein $R_9$ and $R_{10}$ with the nitrogen atom to which they are attached from a heterocyclic ring selected from piperidono, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino and 1-indolinyl rings, said rings being optionally substituted by at least one alkyl radical.

4. A pharmaceutical composition comprising a pharmaceutically effective amount of at least one compound according to claim 1 or a pharmaceutically acceptable salt thereof and a pharmaceutically acceptable carrier.

5. A method for treating disorders related to CCK and to gastrin comprising administering to a patient in need of such treatment an effective amount of a compound according to claim 1 or pharmaceutically acceptable salt thereof.

* * * * *

UNITED STATES PATENT AND TRADEMARK OFFICE
CERTIFICATE OF CORRECTION

PATENT NO. :   5,637,602
DATED      :   June 10, 1997
INVENTOR(S) :  Marc CAPET et al.

It is certified that error appears in the above-indentified patent and that said Letters Patent is hereby corrected as shown below:

In Claim 3, Col. 22, line 52, "from" (first occurrence) should read --form-- ; and "piperidono" should read --piperidino--.

Signed and Sealed this

Ninth Day of December, 1997

Attest:

BRUCE LEHMAN

Attesting Officer

Commissioner of Patents and Trademarks